United States Patent
Schoess

(10) Patent No.: US 6,263,737 B1
(45) Date of Patent: Jul. 24, 2001

(54) ACOUSTIC FAULT INJECTION TOOL

(75) Inventor: Jeffrey Norman Schoess, Buffalo, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/360,015

(22) Filed: Jul. 23, 1999

(51) Int. Cl.[7] ............................................. G01H 1/00
(52) U.S. Cl. .................. 73/583; 73/12.09; 73/12.12; 73/802
(58) Field of Search ............................ 73/12.01, 12.09, 73/12.12, 573, 583, 587, 593, 649, 662, 786, 799, 801, 802, 803, 865.3, 865.6, 432.1, DIG. 1

(56) References Cited

U.S. PATENT DOCUMENTS

| | | | |
|---|---|---|---|
| 3,239,678 | 3/1966 | Kolm et al. ............................. | 307/43 |
| 3,456,134 | 7/1969 | Ko ........................................ | 310/8.5 |
| 3,539,841 | 11/1970 | Riff ...................................... | 310/8.1 |
| 3,585,415 | 6/1971 | Muller et al. .......................... | 310/8 |
| 3,596,269 | 7/1971 | Laska ................................... | 340/421 |
| 4,018,084 | * 4/1977 | Hsu ....................................... | 73/587 |
| 4,033,179 | 7/1977 | Romrell ................................ | 73/71.4 |
| 4,328,441 | 5/1982 | Kroeger, Jr. et al. ................ | 310/319 |
| 4,494,408 | 1/1985 | Delacy .................................. | 73/587 |
| 4,499,394 | 2/1985 | Koal ...................................... | 310/330 |
| 4,524,620 | 6/1985 | Wright et al. ......................... | 73/587 |
| 4,634,917 | 1/1987 | Dvorsky et al. ..................... | 310/328 |
| 4,649,312 | 3/1987 | Robin et al. ......................... | 310/330 |
| 4,685,335 | 8/1987 | Sato et al. ............................ | 73/660 |
| 4,751,418 | 6/1988 | Murase ................................ | 310/319 |
| 4,852,397 | * 8/1989 | Haggag ................................ | 73/82 |
| 4,868,447 | 9/1989 | Lee et al. .............................. | 310/328 |
| 4,901,575 | 2/1990 | Bohannan et al. .................. | 73/587 |

(List continued on next page.)

FOREIGN PATENT DOCUMENTS

| 0443708 | 8/1991 | (EP) . |
| 9304365 | 4/1993 | (WO) . |

OTHER PUBLICATIONS

"It's a Snap", *Electronics.* May 12, 1969.
"Implantable Power Supply", *Design News,* Jun. 7, 1993, p. 54.
Hydromechanic–electric Power Converter by E.Haeusler et al., on pp. 1313–1316 in *Ocean Engineering and Environment,* Conference Record, vol. 2 of 2, Nov. 12–14, 1985 San Diego, CA, IEEE Ocean Engineering Soc.
"Kynar to the Rescue", by Tom Cantrell, on pp. 1–6, in Circuit Cellar Ink *The Computer Applications Journal,* Aug./Sep. 1991, Issue 22.
Article "Rotor Acoustic Monitoring System (RAMS)—A Fatigue Crack Detection System", J.Schoess, F.Malver, B.Iyer, J.Kooyman, Annual Forum Proceedings—American Helicopter Society, V.3, 1997, p.274–281, Copyright 1997 American Helicopter Society. Document No. IPD–P97–015.

*Primary Examiner*—Hezron Williams
*Assistant Examiner*—Rose M. Miller
(74) *Attorney, Agent, or Firm*—John G. Shuby, Jr.

(57) ABSTRACT

A device for generating an acoustic stress wave in metal structures in real-time. A cylindrical housing includes a chamber, a piezostack actuator inside the chamber, and a support ring for relieving strain. The actuator has a high tensile strength block extending therefrom for contacting the surface. A pulse wave generator drives the actuator in accordance with a predetermined frequency to cause micro-indentation and generate an acoustic stress wave in the surface. The stress wave is transmitted to a signal transformer for producing a signal for use in systems for interpreting the signal. In a preferred embodiment, the high tensile block has a ceramic tip for engagement with the surface. The preferred piezostack actuator includes a poled element.

18 Claims, 12 Drawing Sheets

U.S. PATENT DOCUMENTS

| | | | |
|---|---|---|---|
| 4,908,785 | 3/1990 | Cubbins et al. | 364/508 |
| 4,977,516 | 12/1990 | Shepherd | 364/508 |
| 5,014,556 * | 5/1991 | Dunegan | 73/587 |
| 5,165,270 * | 11/1992 | Sansalone et al. | 73/12 |
| 5,176,032 | 1/1993 | Holroyd et al. | 73/587 |
| 5,184,516 | 2/1993 | Blazic et al. | 73/799 |
| 5,191,796 | 3/1993 | Teruso et al. | 73/632 |
| 5,195,046 | 3/1993 | Gerardi et al. | 364/506 |
| 5,245,242 | 9/1993 | Hall | 310/316 |
| 5,270,950 | 12/1993 | Cowley et al. | 364/551.01 |
| 5,293,555 | 3/1994 | Anthony | 364/508 |
| 5,300,875 | 4/1994 | Tuttle | 320/20 |
| 5,317,309 | 5/1994 | Vercellotti et al. | 340/825.54 |
| 5,383,133 | 1/1995 | Staple | 364/508 |
| 5,445,027 | 8/1995 | Zorner | 73/593 |
| 6,014,896 * | 1/2000 | Schoess | 73/583 |
| 6,076,405 * | 6/2000 | Schoess | 73/587 |

* cited by examiner

Tube Extension = $(l/w) \, d_{31}, V,$ where W is the wall thickness.

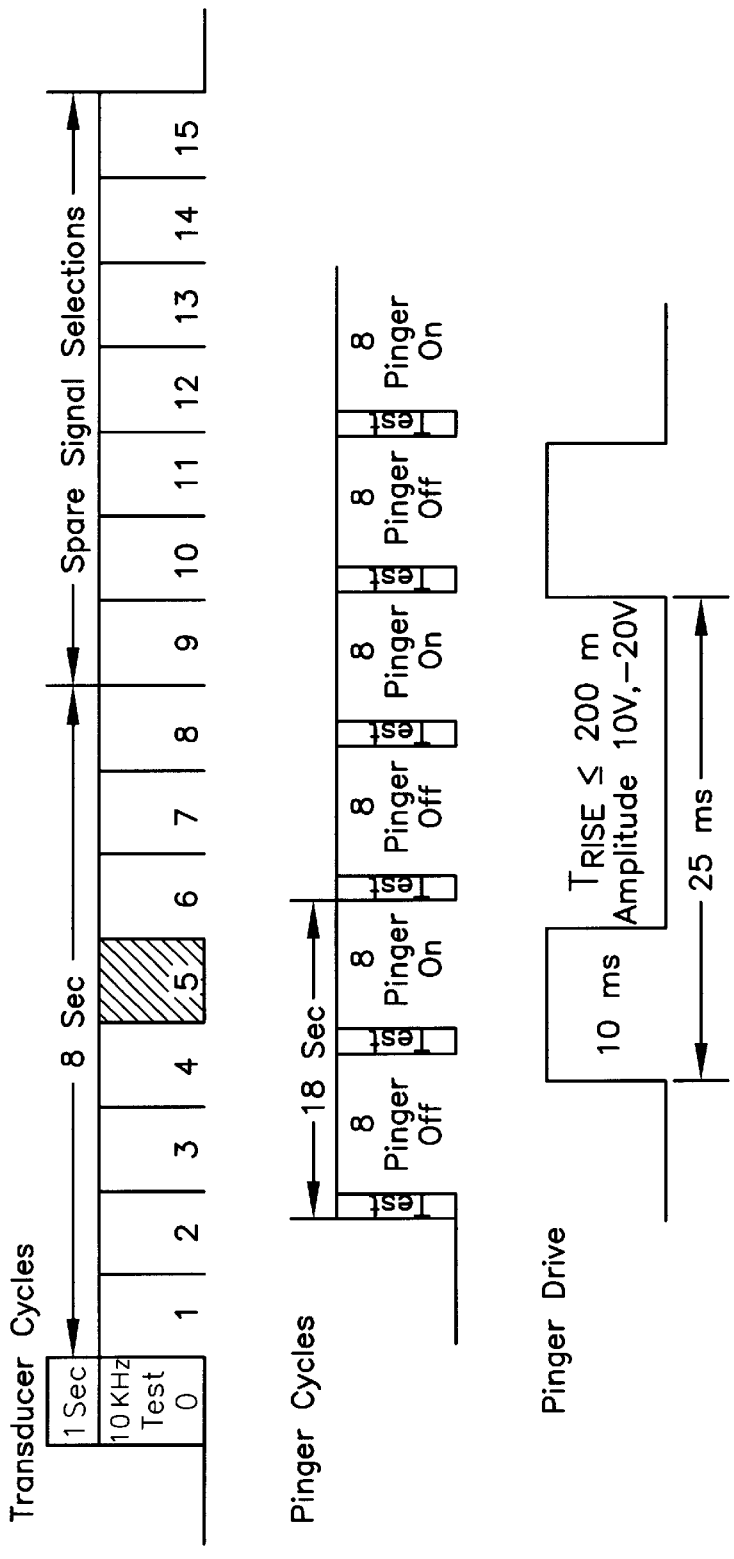
Fig-15 Automatic Acoustic Data Collection

ACOUSTIC FAULT INJECTION TOOL

FIELD OF THE INVENTION

The present invention relates to a device for monitoring helicopter rotor heads to identify fatigue and stress corrosion cracks. More particularly the invention relates to a real-time technique for performing condition-based maintenance and structure health assessment. The Government may have rights in this invention pursuant to Contract No. N00167-94-C-0064, awarded by the Department of the Navy.

BACKGROUND OF THE INVENTION

Real-time monitoring of fatigue and stress corrosion cracks in U.S. Navy helicopter rotor head systems is needed to improve operational safety and permit "condition-based" maintenance and increase operational life. Rotor acoustic monitoring systems have been developed to demonstrate the detection of rotor head fatigue cracks and to investigate the early warning of propagating fatigue cracks. As an example of one helicopter hub, the H-46 Navy helicopter has a fully articulated rotor hub where each rotor blade has three distinct bearings, or degrees of freedom, commonly called hinges, allowing movement the lead/lag direction (fore/aft), offset flapping (up/down) and feathering thrust directions. These three hinges are designed to incorporate metal ball race bearings or elastomeric bearings made of synthetic rubber to minimize rotor head vibration effects. Several factors cause fatigue cracks to initiate and propagate in rotor heads, including: aerodynamic loading forces which cause chord-wise and flap-wise bending; severe corrosion and temperature extreme environments; extended fatigue cycling; and maintenance-induced damage. Rotor head components experience significant fatigue cracks in highly loaded locations such as the main rotor hub, connecting link, pitch shaft, pitch housing, lead/lag dampers, blade fittings, and drive shafts. These cracks can cause catastrophic failure, leading to loss of aircraft and life, and can degrade mode of operation by providing minimal control capability.

Several non-destructive and indirect inspection techniques exist to detect the presence of rotor head cracking, but each method has one or more significant technical limitations. These techniques include visual inspection, tap testing, ultrasound tests, eddy current, x-ray, and magnetic particle tests. Also used as an indirect monitoring approach are blade imbalance and power train monitoring. Visual inspection is most commonly used to check surface conditions such as cracks in main hub assemblies or general surface corrosion, but does little to detect in situ cracks hidden within the bearing retainer area of the connecting link or pitch shaft. Each method has two significant drawbacks, namely: (1) a lack of ability to perform "condition-based" maintenance, requiring manpower to disassemble the rotor assembly and increasing operational costs, limiting in-flight usage, and raising the vulnerability to create maintenance induced faults; and (2) lack of real-time in-flight detection capability, to provide early warning indications of crack initiation or propagation faults. The aerodynamic loads incurred during flight cause the crack initiation and propagation. No existing approach can provide this means of detection.

One system which has been effective in direct monitoring rotor health is set forth in my co-pending patent application entitled REMOTE SELF-POWERED STRUCTURE MONITOR, filed Jul. 24, 1996, and having Ser. No. 08/690,263, now U.S. Pat. No. 6,076,405. In this system, non-repetitive high frequency acoustic emission events from stress wave acoustic emission energy coming from the beginning of structural cracks is converted into electrical signals and processed to provide data, including an alarm. However, in order to demonstrate the efficacy of this self-powered structure monitor, it has now been determined that simulated fatigue cracks should be generated for testing and evaluating purposes. Various methods for generating simulated high frequency stress-wave acoustic fatigue having characteristics consistent with an actual structural fatigue crack have been considered. It is necessary to replicate waveform shape and amplitude as well as frequency content, and it must do so in an environment similar to helicopter rotor head operation conditions.

Accordingly, it would be of great advantage in the art if a device could be provided to generate simulated fatigue cracks in operating rotor hubs and the like.

It would be another great advance in the art if the simulated fatigue cracks could be generated by the device in a remote location, particularly when the structure is being flown or otherwise operated.

Yet another advantage would be if the device would permit an automated real-time technique for injecting acoustic fault phenomena into structures and machinery of interest to perform condition-based maintenance and health assessment.

Other advantages will appear hereinafter.

SUMMARY OF THE INVENTION

It has now been discovered that the above and other objects of the present invention may be accomplished in the following manner. Specifically, the present invention comprises use of a microindentation technique, where a small localized region of the material of interest is loaded rapidly to inject an automated real-time acoustic fault phenomenon into the structure.

A technique comprises the generation of an acoustic stress wave in metal structures in real-time. A housing is mounted on a surface of the structure being monitored. Inside the housing, a piezostack actuator having an end extending therefrom for contacting said surface is activated by a signal from a pulse wave generator with a power amplifier to drive the actuator in accordance with a predetermined frequency. When so driven, the end creates microindentations in the surface to generate an acoustic stress wave at a desired frequency.

The acoustic stress wave is transmitted to one or more signal transformers for producing a signal from said stress wave which is suitable for evaluation during inspection and detection of defects in the structure. Not only is the present invention suitable for inspection and maintenance of aircraft for both fixed wing and helicopter rotating parts, it can be used for any metal or other material capable of transmitting an acoustic stress wave generated by microindentation. The effects of acoustic response to joint load variation is shown below. In addition, the correlation of mechanical loads to machinery performance, as shown herein, permits evaluation of machinery performance and health. Bearing wear, loss of lubrication, corrosion, cracking from aging or excessive use, and other defects can be determined. Railcars and surface transportation are two other areas where the invention is applicable.

BRIEF DESCRIPTION OF THE DRAWINGS

For a more complete understanding of the invention, reference is hereby made to the drawings, in which:

FIG. 5 is a schematic illustration of the principal of operation of the present invention, with an enlarged portion in the area designated with the circle 5a;

FIG. 15 is a schematic illustration of data collection for the preferred embodiment of this invention.

DETAILED DESCRIPTION OF THE PREFERRED EMBODIMENT

Figure 1:
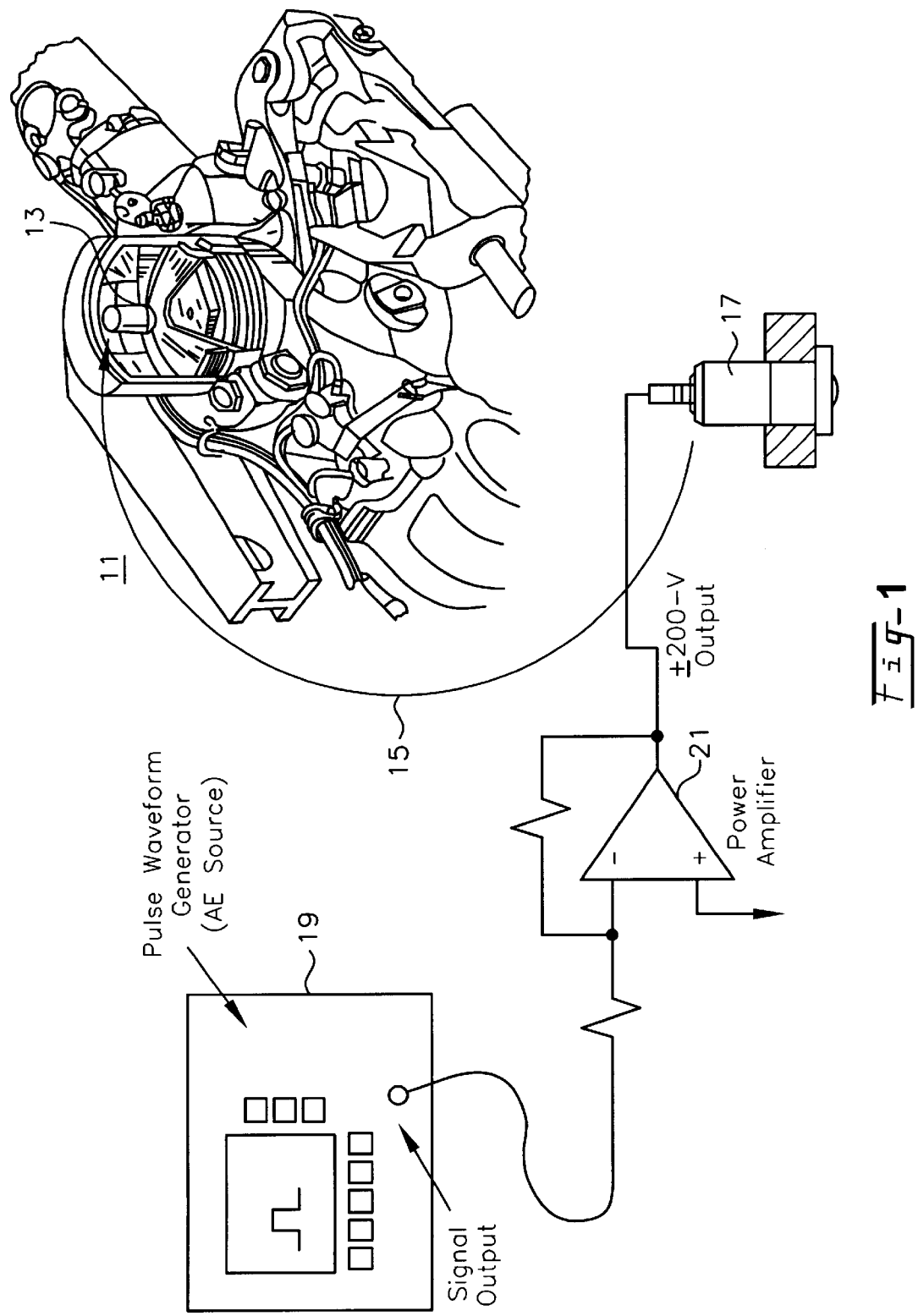
FIG. 1 is a schematic view of the preferred embodiment of the invention shown in use on a helicopter rotor head.

Turning now to the drawings, FIG. 1 illustrates a simplified view of the present invention as implemented for a helicopter rotor head, such as the CH-46 Sea Knight helicopter, 11 generally. Mounted on a rotor head component called the vertical hinge pin cap 13 and removed for illustration purposes by line 15 is a piezo actuator 17, shown in greater detail below. Location of the piezo actuator 17 in the hinge pin cap 13 simulates the effect of a vertical hinge pin bore crack, one such crack occurring at the vertical hinge pin joint. At least one fatal flight accident has been caused by failure of this part.

A pulse waveform generator 19 provides a four-voltage level drive circuit via amplifier 21 with a +/−200 volt output for actuation of actuator 17. The actuator 17 is an off-the-shelf piezostack actuator made by Burleigh, Inc., designated as a PZT pusher, model no. PZ-100. It is presently used to align and position optical components such as mirrors and gratings in optics research to within a five micron displacement.

Figure 2:
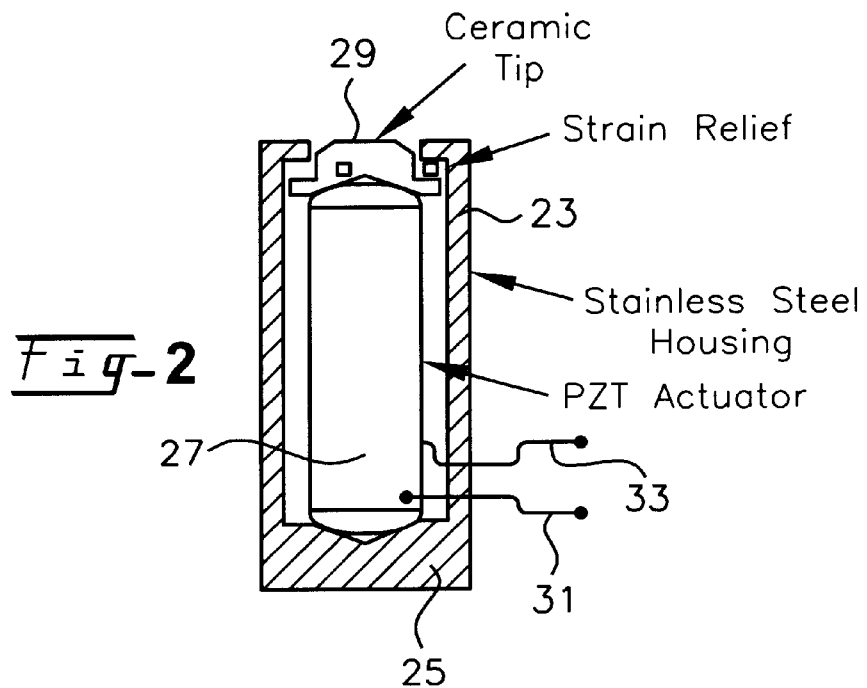
FIG. 2 is a sectioned view of one component of the invention shown in FIG. 1.
Figure 3:
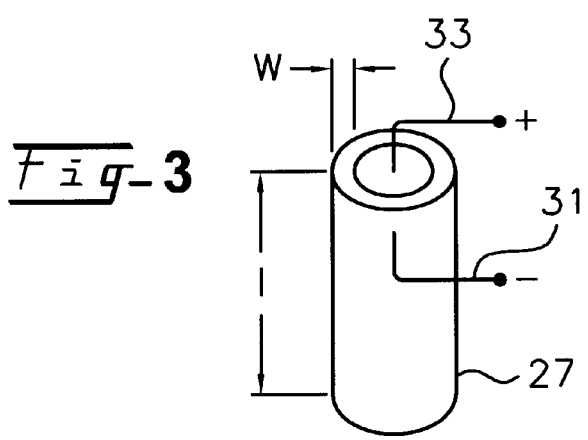
FIG. 3 is a perspective view of another component of the invention shown in FIG. 1.

FIG. 2 illustrates a cross section of the Burleigh product, where the actuator 17 generally includes a stainless steel housing 23 having a base 25 for supporting the piezostack 27 at one end, with a hard ceramic tip 29 extending out from housing 23. Piezostack 27, as seen in FIG. 3, extends and contracts when voltage is applied in relationship to the width and length of the piezoelectric tube which forms piezostack 27. Voltage input 31 and output 33 provide the electrical energy that the piezoelectric material responds to in a mechanical movement, shown more clearly in FIGS. 4a, 4b and 4c.

Figure 4:
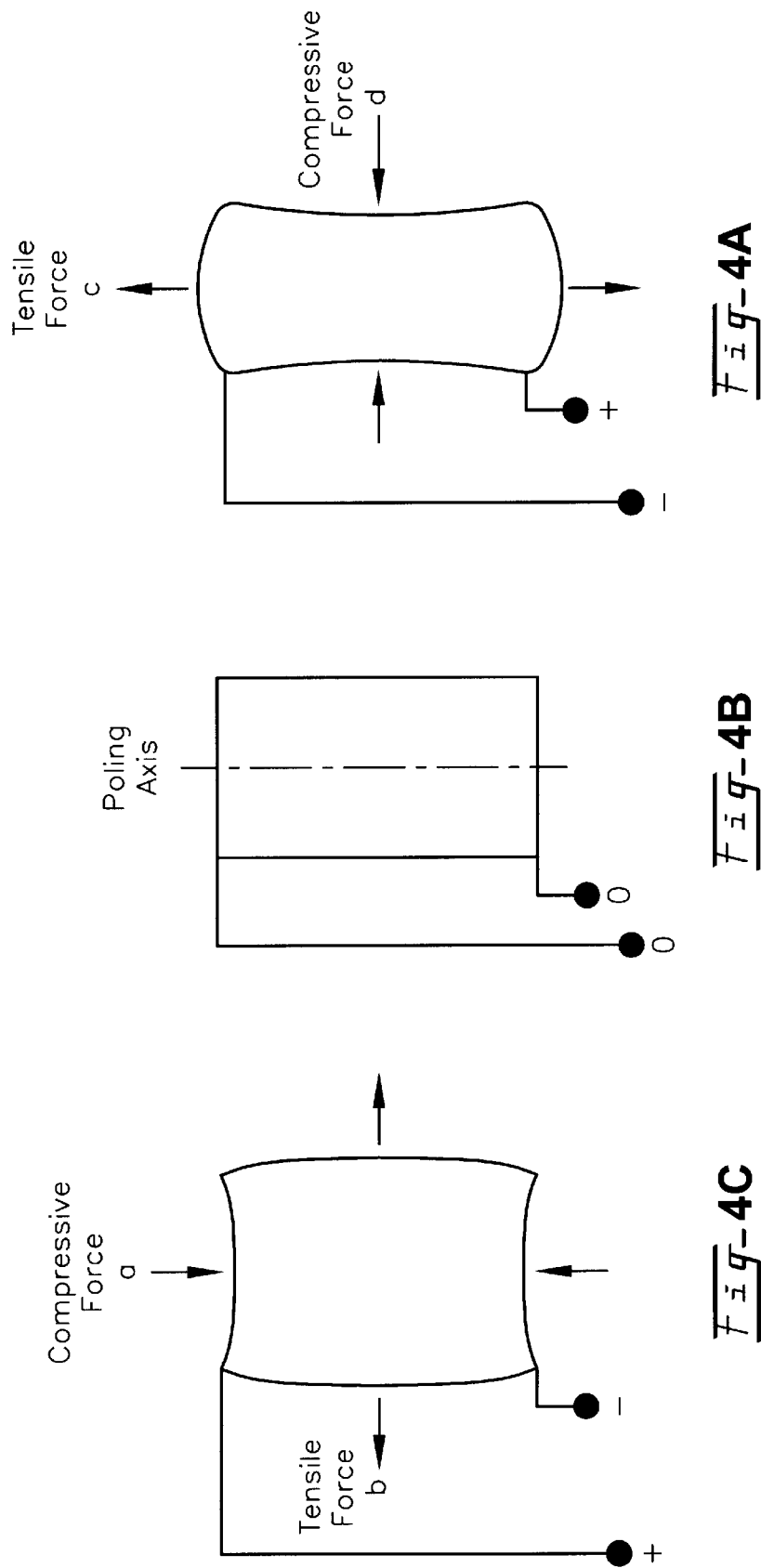
FIGS. 4a, 4b and 4c are three schematic illustrations of the component shown in FIG. 3, under various applied voltages.

FIG. 4b illustrates the poling axis of piezoelectric stack 27, which axis is, of course, aligned along the length of piezostack 27 for movement of ceramic tip 29 of FIG. 2. FIG. 4a illustrates how the piezostack 27 is subjected to a compressive force when the output voltage 33 is the same polarity as piezostack 27. Similarly, FIG. 4c illustrates how the piezostack 27 is subjected to a tensile force when the output voltage 33 is the opposite polarity as piezostack 27. Rapid alternating of the voltage, as described below, will cause similar rapid movement of the ceramic tip 29 into and out of any surface in which tip 29 is in contact with, to create the acoustic patterns in accordance with the invention.

Figure 5:
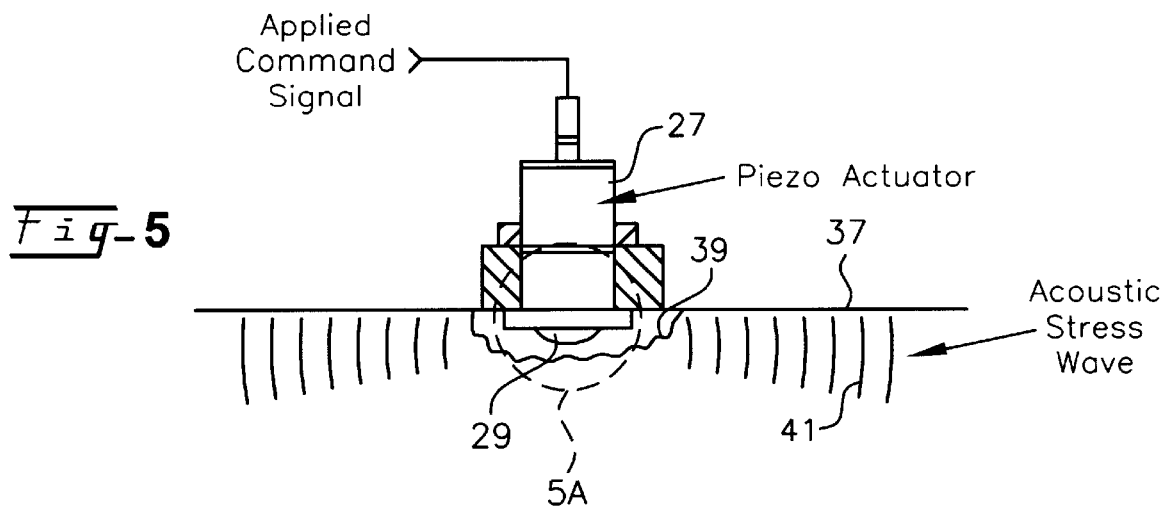
Figure 5A:
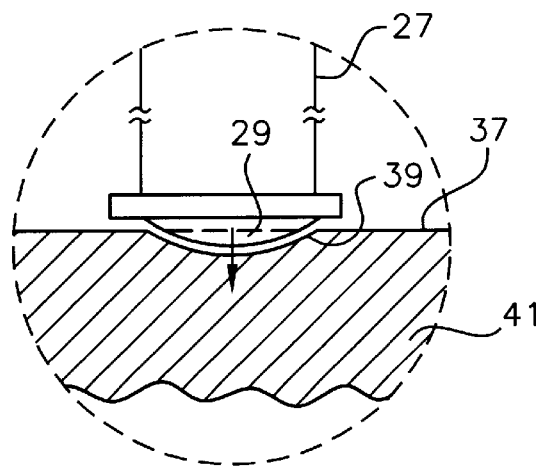

FIG. 5 illustrates the principal of operation of piezostack actuator 27 to generate an applied force below actuator tip 29, when the piezostack 27 is extended, as described above. The localized area on surface 37 is deflected at 39, causing a small change in the surface area. As the piezostack 27 is actuated and extends tip 29, it creates a deflection at the surface 37, then, when tip 29 is rapidly released by movement of piezostack 27 in the opposite direction, a high frequency stress wave acoustic signature 41 is created which propagates in all directions from tip 29 as a simulated event. The amplitude of the event is directly related mathematically to the change in surface area at the point 39 of impact of tip 29.

Figure 6:
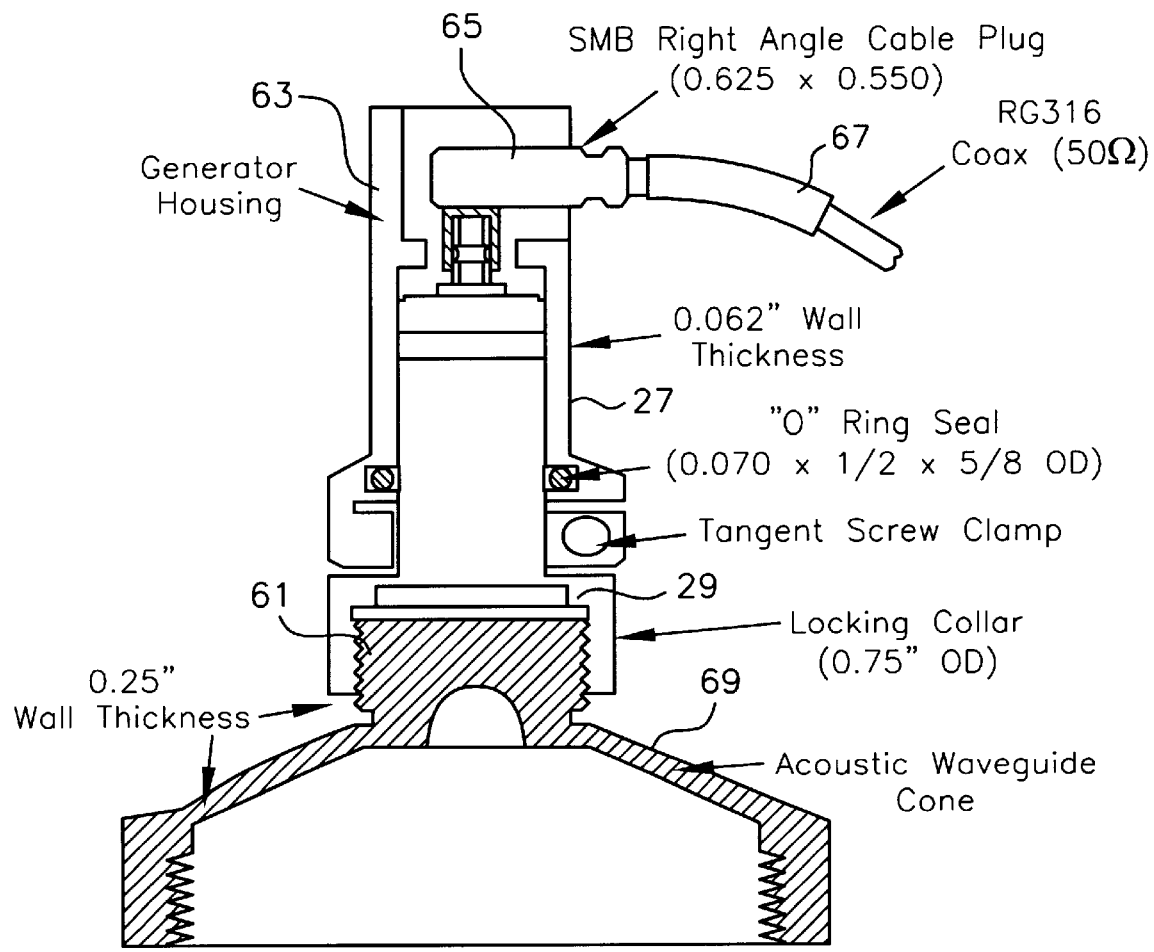
FIG. 6 is an enlarged, partially sectioned, side elevational view of the invention shown in FIG. 1, as mounted on a surface.

FIG. 6 illustrates a simplified cross-sectional view of the rotor mount package of the present invention for use with the vertical hinge pin cover used in test flights using the RAMS flight test as described in my co-pending application entitled REMOTE SELF-POWERED STRUCTURE MONITOR, filed Jul. 24, 1996, and having Ser. No. 08/690,263. Piezostack 27 is mounted on top of hinge pin cover 61 in a support housing 63 which captures the piezostack 27 and provides both mechanical and positioning support, as well as environmental protection. A right angle cable connector 65 is attached on top of housing 63 to provide a command signal via coaxial cable 67 to actuate piezostack 27 and cause ceramic tip 29 to move as described above. The pin cover 61 includes a cone shaped wave guide 69 for transmission of the acoustic stress wave to the appropriate detection and processing equipment for the system in which the present invention is being used.

Figure 7:
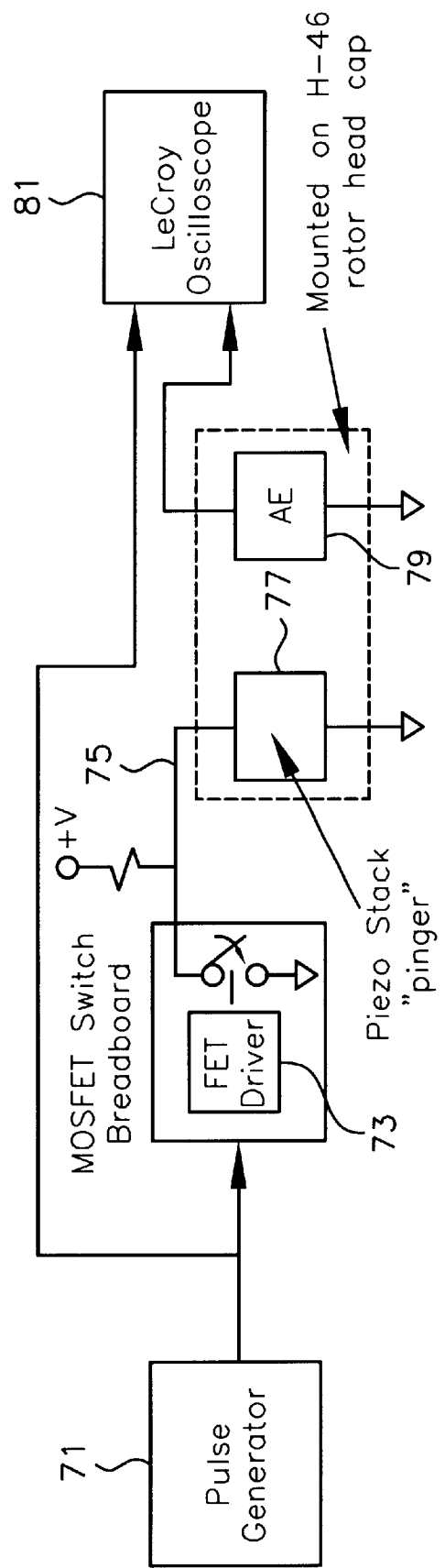
FIG. 7 is a schematic view of a test apparatus demonstrating the efficacy of the present invention.

Drive electronics for the present invention may take a variety of configurations. A pulse generator 71 shown in FIG. 7 incorporates a high speed field-effect transistor (FET) 73 which operates as a switch to generate a bipolar drive signal on line 75. In this configuration, the bipolar drive signal has four selectable output voltages. Used in evaluation of the present invention, as shown in FIG. 7, were output voltages of 100 volts, 48 volts, 20 volts, and 10 volts, which generates unique acoustic waveform signatures, each with an amplitude of 8 to 10 millivolts, 2 to 3 millivolts, 1 millivolt and 0.5 millivolts, respectively. These wave forms and their respective amplitudes correspond with fatigue cracks of different lengths, with the 0.5 millivolt output approximating a fatigue crack of 0.020 inches in length. The piezostack actuator 77 is excited by the applied voltage generated by opening and closing FET switch 73, which electrically grounds the piezostack actuator 77, discharging the capacitance of the piezostack actuator 77 on half of the switching cycle and charging piezostack on the other half of the cycle through a dedicated pull-up resistor, not shown in FIG. 7.

Figure 8:
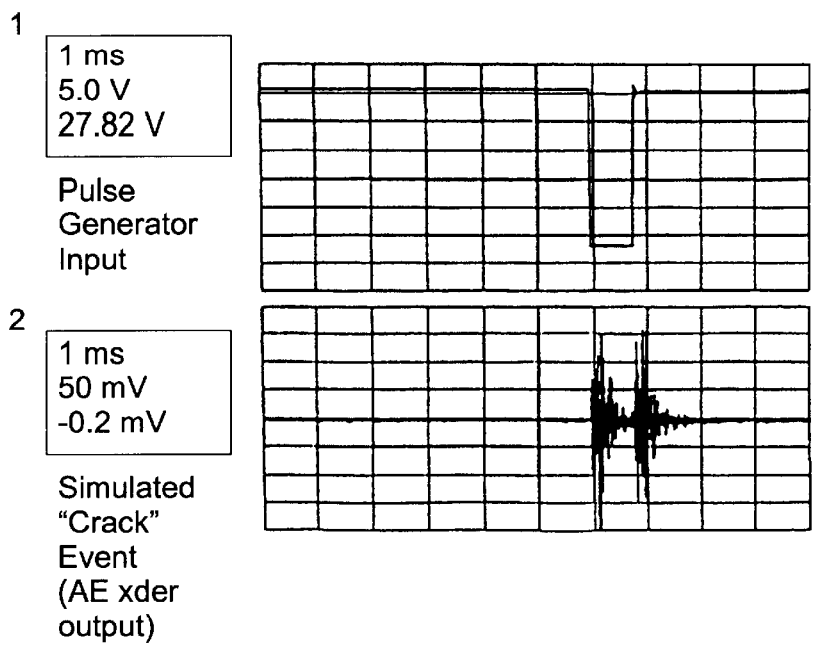
FIGS. 8 and 9 present test data from the apparatus in FIG. 8.
Figure 9:
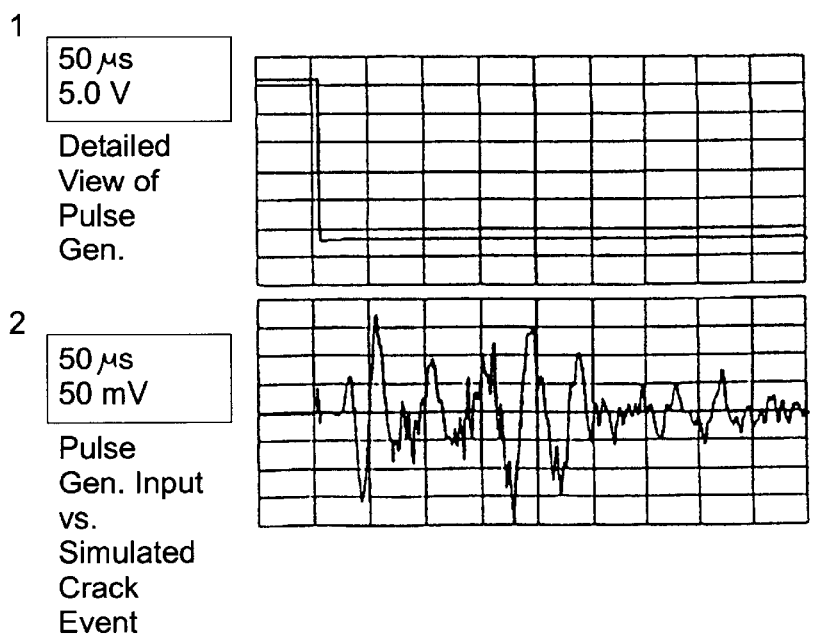

The test arrangement shown in FIG. 7 was used to evaluate the drive electronics and crack generator hardware of the present invention. Actual tests were performed on the vertical hinge pin cap of a retired or scrapped H-46 helicopter rotor head. A wide-bandwidth 5 MHz Harasonics acoustic transducer 79 was mounted on the H-47 rotor cap next to a prototype of the present invention of the type in FIG. 7, to characterize the acoustic response of the piezostack actuator 77. The output of the pulse generator or piezostack actuator 77 was connected to a 1 GHz Lecroy model 9354 digital storage oscilloscope 81. The output of the acoustic transducer 79 was amplified with a 40 dB preamplifier prior to being sampled by the oscilloscope 81. The acoustic wave forms generated by the test are shown in FIGS. 8 and 9, with a unique set of acoustic waveform signatures. The two wave forms correspond with the microindentation properties of the crack generator 77, an unique acoustic event for the falling edge of the pulse waveform which corresponds with the lifting off action of the piezostack tip. The rising edge corresponds with the impacting action of the tip. Each waveform has an unique signature, defined by amplitude, duration, and frequency content, with the lift off action of the piezostack creates an acoustic event having slightly higher spectral content.

Figure 10:
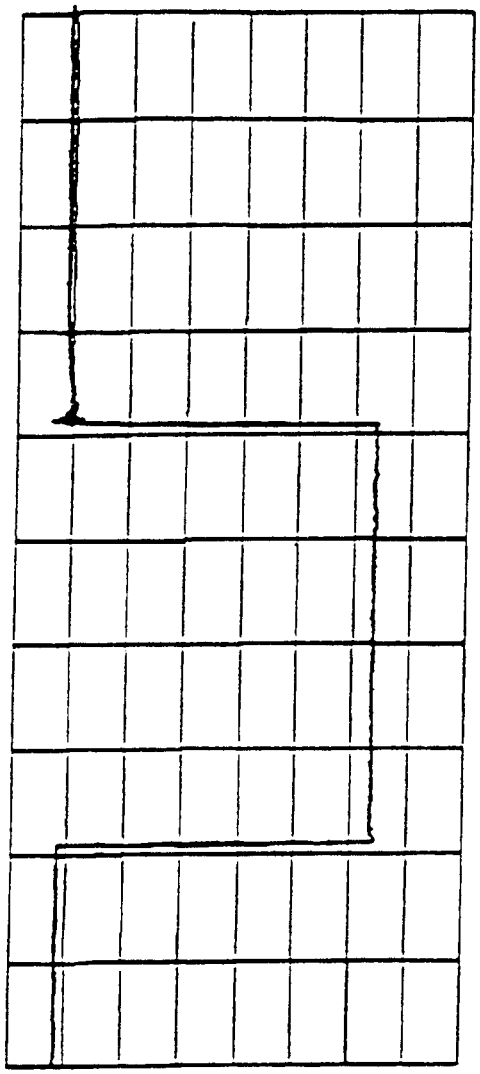
FIGS. 10 and 11 present enlarged test data the apparatus in FIG. 8.
Figure 11:
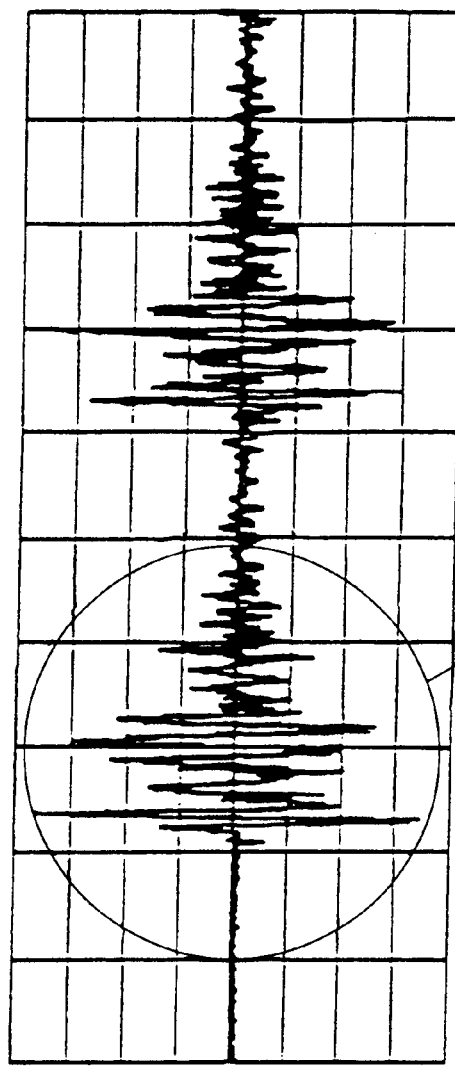

FIGS. 10 and 11 illustrate a detailed view of each simulated acoustic crack event, the lift off action of the piezostack creates an acoustic event having a peak-to-peak amplitude of 1.5 millivolts. This dual mode operation of the crack generator of the present invention, creating two distinct but similar acoustic wave forms with complimentary amplitudes and spectral frequency content is a unique feature of this invention. The two signature wave forms provided the benefits of more robust signal detection and redundancy in measurement during actual RAMS flight tests, potentially minimizing false alarms.

Figure 12:
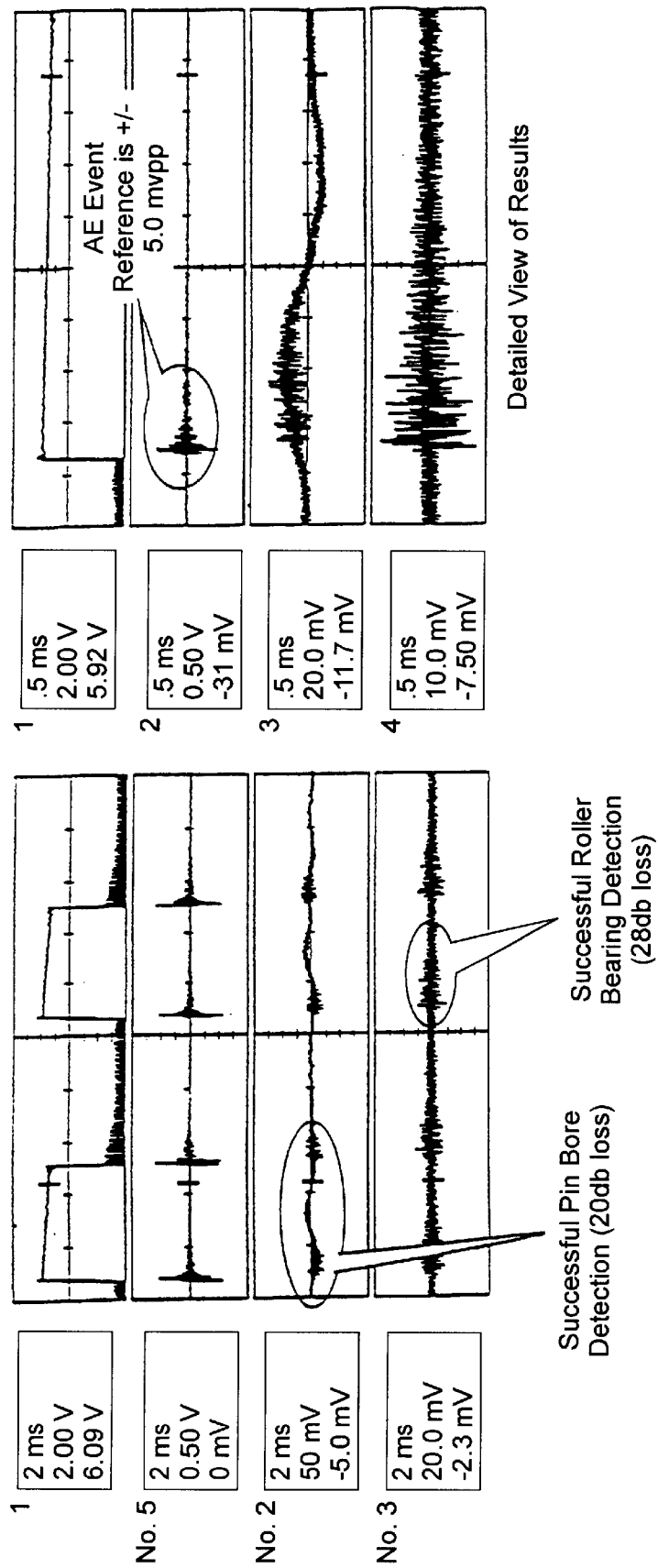
FIG. 12 presents data showing details of a test.
Figure 14:
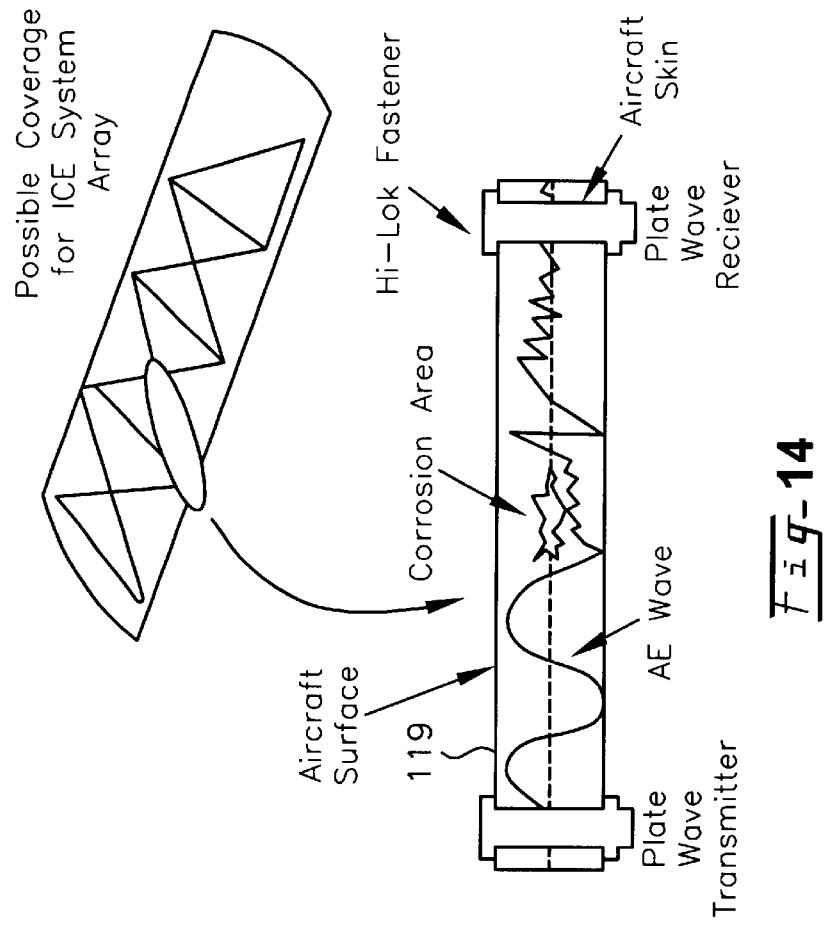
FIG. 14 is a schematic illustration of the application of FIG. 13.

Other subassembly fatigue tests were performed on a complete H-46 rotor arm assembly, including a pitch shaft, connecting link, pitch housing, and blade attach fitting. Simulated centrifugal load forces in excess of 60,000 pounds were introduced via a universal joint. Flap-wise and chord-wise excitation was introduced via two hydraulic RAMS at the respective ends of the fatigue tester. A device according to the present invention was mounted on the top of the vertical hinge pin joint in the same location as described with respect to FIG. 7. The tests accomplished the following objectives: (1) the acoustic energy response of the rotor subassembly under actual fatigue load conditions was assessed; (2) the acoustic energy properties of the rotor head assembly, including transmissibility from one rotor component to another, signal attenuation, background noise effects and their impact on signal detection and recovery during flight tests were characterized; and (3) the performance of the present invention device was evaluated. Examples of these tests are shown in FIG. 12, which summarizes a significant lesson verified by the tests, in that fatigue crack acoustic content can be transmitted through an operational joint. FIG. 14 highlights two sets of plots. The left plot has the command signal issued to the crack generator as the top trace, followed by the acoustic reference signal trace (AE transducer located next to the crack simulator, denoted as transducer number 5) and transducers nos. 2 and 3. The signal traces for transducer no. 2 corresponds with a transducer mounted on the pitch shaft component while transducer no. 3 corresponds with the pitch housing component. The response detected at transducer no. 2 indicates the acoustic energy can be successfully coupled through the vertical hinge pin joint with only 20 dB of signal attenuation. The transducer no. 3 response indicates that acoustic crack energy can be coupled and transmitted even farther away, through the vertical hinge pin and the roller bearing joint of the pitch housing which provides pitch control to the rotor head with only a signal loss of 28 dB. The set of plots on the right-hand side of FIG. 12 provides a more detailed view of the test results.

Figure 13:
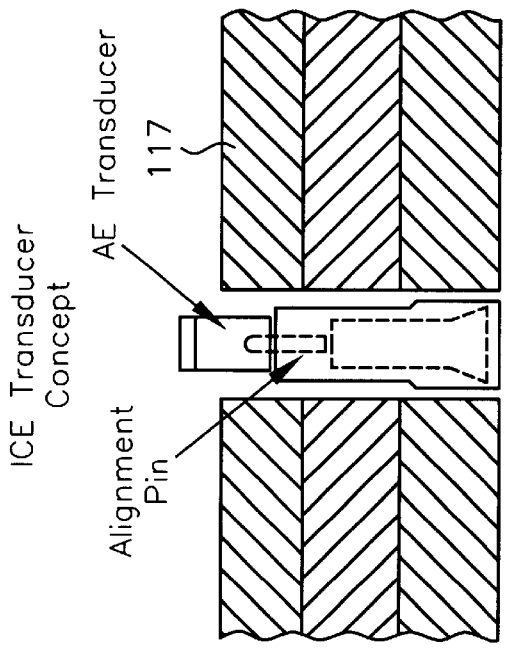
FIG. 13 is a sectioned view of another application of the present invention.

The device of the present invention may also be used for reliable inspection and detection of hidden and inaccessible damage in aging structures such as aircraft skins, bridges, and the like. Corrosion, particularly when there is loss of structural integrity, is a major concern. FIG. 13 illustrates the use of an acoustic energy transmitter 117 mounted in the aircraft skin 119 to project acoustic energy into the lap joint toward the damaged area. One or more acoustic receivers would detect and capture the transmitted energy and examine transmitted verses reflected energy to determine material loss and location of the hidden structural damage. FIG. 14 illustrates this concept.

FIG. 15 illustrates an automatic acoustic data collection which highlights the timing pattern during operation of the invention. The transducer cycles are shown operating at one second, where the pinger cycles are also shown. The pinger drive is on for 10 ms over a time of 25 ms, with a rise time less than or equal to 200 ns. FIG. 15 illustrates the time allowed to allow the simulated crack energy to propagate through the rotor head structure after it is injected, and time to collect background noise.

Figure 16:
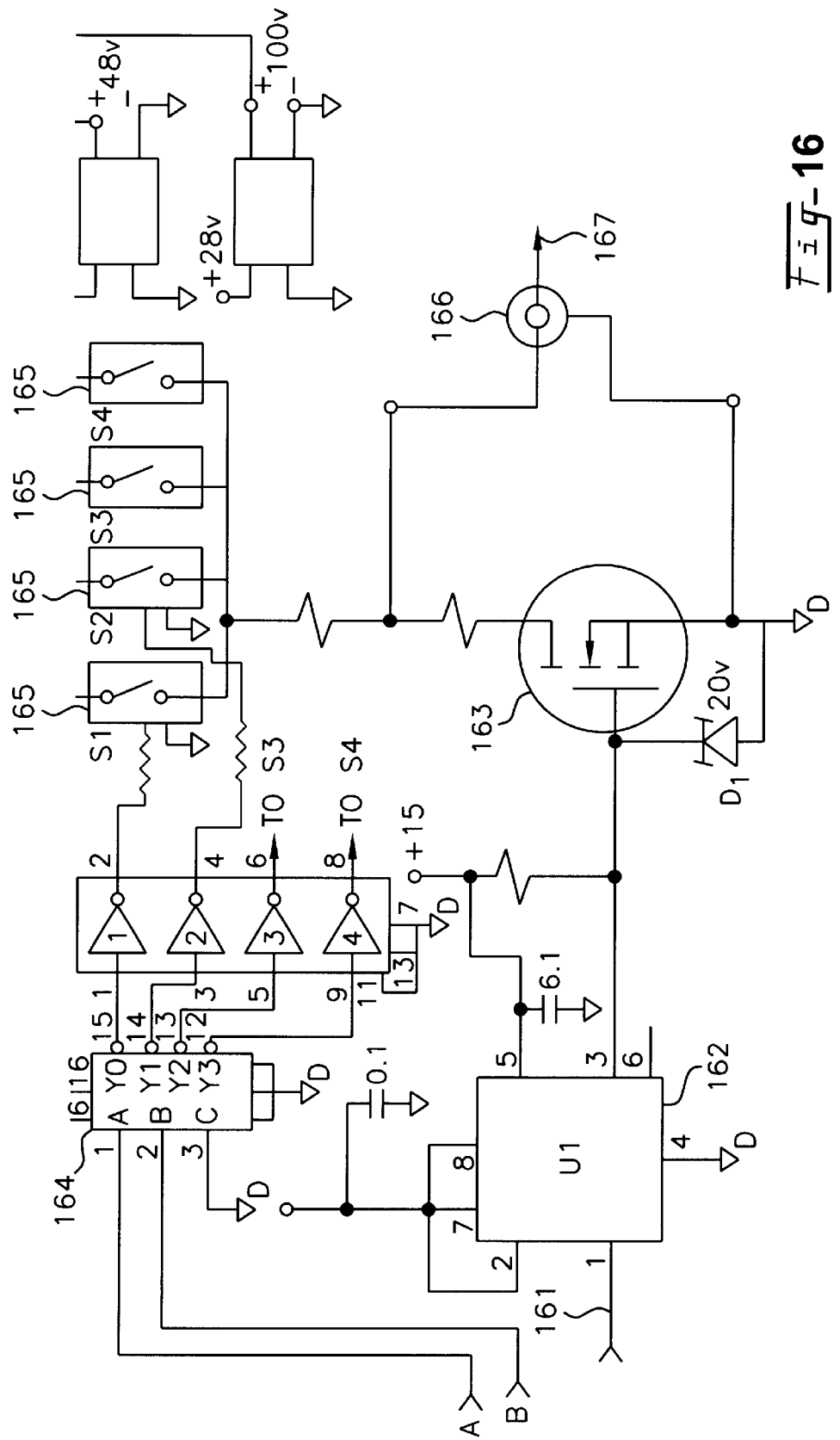
FIG. 16 is a schematic circuit diagram of the FET shown in FIG. 7 and is a crack generator drive circuit producing the cycles of operation for the preferred embodiment.

FIG. 16 illustrates schematically the drive electronics for the present invention in its preferred embodiment. In FIG. 16, the schematic summarizes a design incorporating a high speed field-effect transistor operating as a switch to generate a bipolar drive signal. As noted with FIG. 7, the FET 73 operates as a switch to generate a bipolar drive signal on line 75. To get the proper logic levels and sequences, the device functions effectively with the circuit in FIG. 16. A drive signal 161 enters IC drive 162 from a general drive device, not shown, to drive the FET 163. Decoder 164 feeds four opto solid state switches 165 connected in series to get the desired voltages of 10 volts, 20 volts, 48 volts and 100 volts, which are then sent to the piezo stack or pinger via junction 166 and line 167. All of the elements shown in FIG. 16 are off-the-shelf circuit elements.

While particular embodiments of the present invention have been illustrated and described, it is not intended to limit the invention, except as defined by the following claims.

What is claimed is:

1. A device for generating an acoustic stress wave in metal structures in real-time, comprising:
   a housing having a chamber;
   a piezostack actuator mounted inside said housing, said actuator having an end extending therefrom for contacting a surface;
   a support ring positioned to relieve stress between said chamber and said actuator;
   a source of electrical energy connected to said actuator to drive said actuator to cause microindentation in said surface and thereby generate an acoustic stress wave in said surface; and
   a connection transmitting said acoustic stress wave to a signal transformer for producing a signal from said stress wave.

2. The device of claim 1, wherein said end comprises a high tensile block having a ceramic tip for engagement with said surface.

3. The device of claim 1, wherein said end is adapted to move a distance of from about 3 to about 7 $\mu$m over application of a voltage of up to 1000 volts.

4. The device of claim 1, wherein said piezostack actuator includes a poled element having a poling axis, said actuator generating a tensile force along said axis when the output voltage of said actuator is the opposite polarity as said poled element and compressive force when the output voltage of said actuator is the same polarity as said poled element.

5. A device for generating an acoustic stress wave in metal structures in real-time, comprising:

a cylindrical housing having a chamber;

a piezostack actuator mounted inside said housing chamber, said actuator having a high tensile strength block extending therefrom for contacting a surface, said chamber and actuator including a support ring for relieving strain between said chamber and said actuator;

a pulse wave generator and power amplifier connected to said actuator to drive said actuator in accordance with a predetermined frequency to cause microindentation in said surface and thereby generate an acoustic stress wave in said surface at a desired frequency; and a connection transmitting said acoustic stress wave to a signal transformer for producing a signal from said stress wave.

6. The device of claim 5, wherein said high tensile block includes a ceramic tip for engagement with said surface.

7. The device of claim 5, wherein said end is adapted to move a distance of from about 3 to about 7 µm over application of a voltage of up to 1000 volts.

8. The device of claim 5, wherein said piezostack actuator includes a poled element having a poling axis, said actuator generating a tensile force along said axis when the output voltage of said actuator is the opposite polarity as said poled element and compressive force when the output voltage of said actuator is the same polarity as said poled element.

9. The device of claim 5, wherein said metal structure is a rotating part of an aircraft.

10. A device for generating an acoustic stress wave in metal structures in real-time, comprising:

housing means having a housing chamber;

piezostack actuator means mounted inside said housing chamber for movement therein, said actuator means having a high tensile strength block means extending therefrom for contacting a surface, said housing means and said actuator means including strain relief means for relieving strain therebetween;

pulse wave generator means for driving said actuator means at a predetermined frequency to cause microindentation in said surface by said block means to thereby generate an acoustic stress wave in said surface at a desired frequency; and connection means for transmitting said acoustic stress wave to a signal receiver means for processing said signal.

11. The device of claim 10, wherein said high tensile block means includes ceramic tip means for engagement with said surface.

12. The device of claim 11, wherein said ceramic tip means is adapted to move a distance of from about 3 to about 7 µm over application of a voltage of up to 1000 volts.

13. The device of claim 10, wherein said piezostack actuator means includes a poled element having a poling axis, said actuator means generating a tensile force along said axis when the output voltage of said actuator is the opposite polarity as said poled element and compressive force when the output voltage of said actuator is the same polarity as said pled element.

14. The device of claim 10, wherein said metal structure is a rotating part of an aircraft.

15. A method of generating an acoustic stress wave in metal structures in real-time, comprising the steps of:

mounting a housing including a chamber on a surface of said structure;

positioning a piezostack actuator inside said housing chamber, said actuator having an end extending therefrom for contacting said surface;

relieving stress between said chamber and said actuator using a support ring;

causing a pulse wave generator and power amplifier to drive said actuator in accordance with a predetermined frequency to cause said end to created microindentations in said surface to generate an acoustic stress wave in said surface at a desired frequency; and transmitting said acoustic stress wave to a signal transformer for producing a signal from said stress wave.

16. The method of claim 15, wherein said end comprises a high tensile block having a ceramic tip for engagement with said surface.

17. The method of claim 15, wherein said end is moved a distance of from about 3 to about 7 µm over application of a voltage of up to 1000 volts.

18. The method of claim 15, wherein said piezostack actuator includes a poled element having a poling axis, said actuator generating a tensile force along said axis when the output voltage of said actuator is the opposite polarity as said poled element and compressive force when the output voltage of said actuator is the same polarity as said poled element.

* * * * *